United States Patent [19]

Chang et al.

[11] 4,062,905
[45] Dec. 13, 1977

[54] MANUFACTURE OF LIGHT OLEFINS

[75] Inventors: Clarence D. Chang, Princeton; William H. Lang, Pennington, both of N.J.; Anthony J. Silvestri, Morrisville, Pa.

[73] Assignee: Mobil Oil Corporation, New York, N.Y.

[21] Appl. No.: 747,581

[22] Filed: Dec. 6, 1976

Related U.S. Application Data

[60] Continuation-in-part of Ser. No. 710,967, Aug. 2, 1976, which is a continuation-in-part of Ser. No. 691,959, June 1, 1976, abandoned, which is a division of Ser. No. 537,043, Dec. 27, 1974, abandoned, which is a continuation-in-part of Ser. No. 387,222, Aug. 9, 1973, Pat. No. 3,894,106.

[51] Int. Cl.$^2$ .................................................. C07C 1/20
[52] U.S. Cl. ......................................................... 260/682
[58] Field of Search .............................................. 260/682

[56] References Cited

U.S. PATENT DOCUMENTS 3,894,106  7/1975  Chang et al. .................... 260/668 R

*Primary Examiner*—C. Davis
*Attorney, Agent, or Firm*—Charles A. Huggett; Raymond W. Barclay

[57] ABSTRACT

A catalytic process is provided for converting a charge consisting essentially of methanol, dimethyl ether or mixtures thereof to a hydrocarbon product rich in ethylene and propylene by contact, under conversion conditions, with a catalyst comprising a crystalline aluminosilicate zeolite characterized by pores, the major dimension of which is less than 6 Angstroms and the capability, under said conditions, of producing less than 20 weight percent methane in said hydrocarbon product.

12 Claims, No Drawings

MANUFACTURE OF LIGHT OLEFINS

CROSS REFERENCES TO RELATED APPLICATIONS

This application is a continuation-in-part of application Ser. No. 710,967 filed Aug. 2, 1976 which in turn is a continuation-in-part of application Ser. No. 691,959 filed June 1, 1976, now abandoned which in turn is a division of application Ser. No. 537,043 filed Dec. 27, 1974, now abandoned, which in turn is a continuation-in-part of application Ser. No. 387,222 filed Aug. 9, 1973 and now U.S. Pat. No. 3,894,106.

BACKGROUND OF THE INVENTION

1. Field of the Invention

This invention relates to a process for the conversion of methanol, dimethyl ether or mixtures thereof to light olefins in the presence of a particularly characterized small pore crystalline aluminosilicate zeolite-containing catalyst.

2. Description of the Prior Art

U.S. Pat. No. 3,036,134 to Mattox discloses conversion of methanol to a reaction product containing water and dimethyl ether in the presence of a sodium or calcium crystalline aluminosilicate zeolite catalyst.

U.S. Pat. No. 3,529,033 to Frilette and Weisz discloses dehydration of a normal alkanol of three to six carbon atoms to an olefin, utilizing a sodium or calcium crystalline aluminosilicate zeolite catalyst having uniform interstitial dimensions sufficiently large to admit the alkanol charge and to permit egress therefrom of the olefin product.

The prior art, typified by the above patents, has, to the best of applicants' knowledge, neither disclosed nor recognized the advantages of a process for selectively converting methanol, dimethyl ether or mixtures thereof to $C_2$-$C_3$ olefins utilizing the small pore crystalline aluminosilicate zeolite catalyst described herein.

As those in the art are aware, a remarkable growth in the production of synthetic fibers, plastics and rubber has taken place in recent decades. Their growth, to a very large extent, has been supported and encouraged by an expanding supply of inexpensive petroleum raw materials such as ethylene and propylene. Increasing demand for these light olefins has, from time to time, led to periods of shortage, either due to a diminished supply of suitable feedstocks or to limited processing capacity. In any event, it is considered highly desirable to provide efficient means for converting raw materials other than petroleum to light olefins.

SUMMARY OF THE INVENTION

In accordance with the present invention, there has been discovered a process which selectively produces valuable light olefinic hydrocarbons. The present process involves conversion of methanol, dimethyl ether or mixtures thereof by contact at elevated temperatures with a catalyst comprising a crystalline aluminosilicate zeolite having pores, the major dimension of which is less than 6 Angstroms, said zeolite further being characterized by the ability to produce a hydrocarbon product containing less than 20 weight percent of methane.

It has been found that use of such zeolite catalysts affords a substantially higher selectivity for ethylene and propylene production over corresponding use of crystalline aluminosilicate zeolites not possessing these characteristics. It has further been found utilizing the specified small pore crystalline aluminosilicate zeolite catalyst described herein that the $C_2$-$C_3$ olefin content of the reaction product obtained can be in excess of 35 weight percent and preferably constitute a major proportion of such reaction product. The latter is substantially devoid of aromatic hydrocarbon content and contains, as a result of employing the specified catalyst, less than 20 weight percent, and preferably not more than 10 weight percent, of methane.

The methanol feedstock may be manufactured from synthesis gas, i.e., mixture of CO and $H_2$, from coal or may be produced by fermentation.

The present process comprises conversion of methanol, in the presence of the specified catalyst at a temperature between about 500° F. and about 1100° F. at a pressure between about 0.2 and about 30 atmospheres and preferably at atmospheric pressure utilizing a feed liquid hourly space velocity (LHSV) between about 0.1 and about 200 and preferably between about 1 and about 20, said operating conditions being selected to produce olefins boiling below $C_5$ hydrocarbons. The latter LHSV is based upon the volume of catalyst composition, i.e., total volume of active catalyst and binder therefor. The effluent is separated and distilled to remove the desired products of light olefinic hydrocarbons. Any unreacted charge may be recycled for further reaction.

DESCRIPTION OF SPECIFIC EMBODIMENTS

It is contemplated that methyl alcohol, dimethyl ether or mixtures thereof may be used as feed to the process of this invention. Such feed, in accordance with this invention, is brought into contact, under the aforenoted conversion conditions, with a bed comprising particle-form catalyst containing a crystalline aluminosilicate zeolite (1) characterized by pores the major dimension of which is less than 6 Angstroms and (2) having the capability, under such conversion conditions, of producing a hydrocarbon product containing less than 20 weight percent of methane.

The zeolites utilized herein may be either naturally occurring or synthetic and include, by way of example, erionite, chabazite, zeolite T and zeolite ZK-5. Zeolite T is described in U.S. Pat. No. 2,950,952 and zeolite ZK-5 in U.S. Pat. No. 3,247,195. The crystal structure of the class of zeolites suitable for use as catalysts in the process of this invention is such as to provide access to and egress from the intracrystalline free space of the zeolites by virtue of having pores, the major dimension of which is greater than 3 but less than 6 Angstrom units. The zeolites utilized herein are further characterized by pore windows of about a size such as would be provided by 8-membered rings of oxygen atoms. It will be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. The pores characterizing the zeolites useful in the present process may be substantially circular, such as in zeolite ZK-5 having uniform pores of about 3.9 Angstroms or somewhat elliptical, such as in erionite having pores of approximately 3.6 by 5.2 Angstroms. It will be understood that, in any case, the zeolites used as catalysts in the process of this invention have a major pore dimension of less than 6 Angstroms. The pore size dimensions of the above zeolites, as well as other feasible zeolites, are those specified in "Zeolite Frameworks" by W. M. Meier and D. H. Olson appearing in Advances in Chemistry Series, Vol. 101, Pages 155–170 (1971), the contents of which are incorporated herein by reference.

In addition to having the hereinabove described pore size characteristics, the crystalline aluminosilicate zeolite utilized as catalyst in the present process should have the capability of producing a hydrocarbon product containing less than 20 percent and preferably not more than 10 percent by weight of methane. Thus, the calcium form of zeolite A, having pores of approximately 5 Angstroms and commonly referred to as zeolite 5A, while satisfying the pore size requirements for zeolites useful as catalysts in the process described herein, is nevertheless, not a particularly feasible catalyst since under the conversion conditions utilized in such process, this zeolite produces considerable amounts of methane, i.e. far in excess of the specified maximum of 20 weight percent characterizing the crystalline aluminosilicate zeolites which have been found to be effective in selectively converting methanol and/or dimethyl ether to ethylene and propylene.

The zeolites useful in the conversion process of this invention generally have at least 10 percent of the cationic sites thereof occupied by ions other than alkali or alkaline earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g. ammonium ions, which upon calcination yield the hydrogen form. This exchange is conveniently carried out by contact of the zeolite with an ammonium salt solution, e.g. ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

In practicing the desired conversion process, it may be desirable to incorporate the above-described small pore crystalline aluminosilicate zeolites in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the small pore zeolites employed herein may be compounded with a porous matrix material, such as alumina, silica-alumina, silica-magnesia, silica-zironia, silica-thoria, silica-beryllia, silica-titania, as well as ternary combinations, such as silica-alumina-thoria, silica-alumina-zirconia, silica-alumina-magnesia and silica-megnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

The process of this invention is conducted such that methyl alcohol and/or dimethyl ether conversion is carried out in the vapor phase by contact in a reaction zone, such as for example, a fixed bed of catalyst, under effective conversion conditions. Such conditions include an operating temperature between about 500° F. and about 1100° F., a pressure between about 0.2 and about 30 atmospheres and preferably atmospheric pressure and a liquid hourly space velocity between about 0.1 and about 200 and preferably between about 1 and about 20. Carrier gases or diluents may be injected into the reaction zone such as, for example, hydrogen or nitrogen.

The methyl alcohol and/or dimethyl ether conversion process described herein may be carried out as a batch-type, semi-continuous or continuous operation utilizing a fixed or moving bed catalyst system. A preferred embodiment entails use of a catalyst zone wherein the alcohol or ether charge is passed concurrently or countercurrently through a moving bed of particle-form catalyst. The latter after use is conducted to a regeneration zone wherein coke is burned from the catalyst in an oxygen-containing atmosphere, e.g., air, at an elevated temperature, after which the regenerated catalyst is recycled to the conversion zone for further contact with the alcohol and/or ether feed.

The product stream in the process of the invention contains steam and a hydrocarbon mixture of paraffins and olefins, substantially devoid of aromatics. This mixture is particularly rich in light olefins, i.e., ethylene and propylene. Generally, a major fraction of the total olefins is ethylene plus propylene. Thus, the predominant hydrocarbon product constitutes valuable petrochemicals. The steam and hydrocarbon products are separated from one another by methods well known in the art.

The following examples will serve to illustrate the process of this invention without limiting the same. Conversions are based on [$CH_2$] content of the feed, i.e. the content of carbon and hydrogen after elimination of oxygen as water.

EXAMPLE 1

Ammonium erionite (40 grams) and ethylenediaminetetraacetic acid (30 grams) were placed in a 500 ml. flask equipped with a large extractor and reacted for about 39 days at about 100° C. The resulting solution, essentially neutral, was filtered and the filter cake water washed to yield 31 grams of dealuminized erionite having the following composition and properties:

|  | Weight Percent |
|---|---|
| Silica | 86.5 |
| Alumina | 9.0 |

-continued

| | Weight Percent |
|---|---|
| Sodium | <0.01 |
| Calcium | 0.01 |
| Magnesium | <0.01 |
| Potassium | 1.8 |
| Silica/Alumina | 16.3 |
| Hexane Sorption | 7.4 |
| Cyclohexane Sorption | 0.4 |

EXAMPLE 2

Methanol was conducted over a bed of the dealuminized erionite zeolite catalyst prepared as in Example 1 at a temperature of 700° F., atmospheric pressure and a liquid hourly space velocity of 1. Analyses of the reaction product showed the following results:

| Conversion (Wt.%) | 9.6 |
|---|---|
| Hydrocarbon Distribution (Wt.%) | |
| Methane | 5.5 |
| Ethane | 0.4 |
| Ethylene | 36.3 |
| Propane | 1.8 |
| Propylene | 39.1 |
| Butanes | 5.7 |
| Butenes | 9.0 |
| $C_5^+$ | 2.2 |

EXAMPLE 3

Erionite ore (500 grams) was refluxed overnight in 1300 ml. of a 5 Normal aqueous solution of NH$_4$Cl. The product was filtered and then refluxed 4 hours in 1300 ml of 5 Normal NH$_4$Cl. The resulting product was filtered and washed with 2 liters of water. Thereafter, the product was slurried in 2 liters of water, filtered and washed again with an additional 2 liters of water. The resulting ammonium form erionite was calcined at 5° F per minute to a temperature of 572° F, held at such temperature for 3 hours and then heated at 5° F per minute to a temperature of 1000° F for 3 hours.

Methanol conversion with the above prepared hydrogen form erionite as catalyst was carried out using a pulse microreactor. The reaction zone contained 50 milligrams of a 60/80 mesh sample of the catalyst. Methanol (1 micro liter) was injected into a stream of helium, which functioned as a carrier gas, flowing through the reactor at 25 cc/minute and then directly into the sampling port of a gas chromatograph. Analyses of the resulting reaction product are hereinafter set forth in Table I.

EXAMPLE 4

Chabazite (60 cc corresponding to about 40 grams) in the form of 8 - 12 mesh particles was ammonium exchanged by contacting with a 5 Normal aqueous solution of NH$_4$Cl at reflux conditions over a weekend. The resulting exchanged product was water washed and dried. The ammonium form chabazite so obtained was calcined at 5° F per minute to a temperature of 572° F, held at such temperature for 3 hours and then heated at 5° F per minute to a temperature of 1000° F for 3 hours.

Methanol conversion using the above prepared hydrogen form chabazite as catalyst was carried out employing the technique described in Example 3. Analyses of the reaction product obtained are shown in Table I.

EXAMPLE 5

Zeolite ZK-5 was prepared following the procedure described in U.S. 3,247,195. After ammonium exchange and calcination, the resulting hydrogen form zeolite ZK-5 was used as catalyst for methanol conversion employing the technique described in Example 3. Analyses of the reaction product are set forth in Table I.

TABLE I

| Example | 3 | 4 | 5 |
|---|---|---|---|
| Catalyst | Erionite | Chabazite | ZK-5 |
| Temperature ° F | 1000 | 1000 | 800 |
| Conversion (wt.%) | 100 | 100 | 100 |
| Hydrocarbon Distribution (wt. %) | | | |
| Methane | 11.0 | 3.3 | 3.2 |
| Ethane | 5.0 | 4.4 | 0 |
| Ethylene | 26.7 | 25.4 | 21.4 |
| Propane | 27.0 | 33.3 | 31.8 |
| Propylene | 18.8 | 21.2 | 13.5 |
| $C_4$ | 9.6 | 10.4 | 22.6 |
| $C_5^+$ | 1.9 | 2.0 | 7.5 |

EXAMPLES 6 - 8

A number of small pore crystalline aluminosilicate zeolites were prepared for catalytic evaluation by refluxing the zeolite in 5N NH$_4$CL (10 cc solution/gram of zeolite) for 20 hours, followed by similar treatment with fresh solution for 4 hours, filtering, air drying and air calcination at 1° C/minute to 538° C then retained for 7 hours at 538° C.

Methanol was pumped at a liquid hourly space velocity of 1.5 through a 1 gram bed of 14-30 mesh catalyst sample. The reaction was carried out at 370° C (518° F) and at atmospheric pressure. The hydrocarbon product distribution was determined by gas chromatography and the results set forth in Table II below:

TABLE II

| Example | 6 | 7 | 8 |
|---|---|---|---|
| Catalyst | Chabazite | Erionite | Erionite De-Aluminized[c] $SiO_2:al_2O_3 = 10:1$ |
| Conversion (Wt.%) | 3[a] | 5[a] | 80[b] |
| Hydrocarbon Distribution (Wt.%) | | | |
| Methane | 10 | 6 | 2 |
| Ethane | 14 | 5 | 1 |
| Ethylene | 32 | 44 | 46 |
| Propane | 2 | 1 | 2 |
| Propylene | 31 | 33 | 26 |
| Butanes | 1 | 1 | 4 |
| Butenes | — | 8 | 10 |
| $C_5^+$ | 9 | 2 | 9 |

[a]One hour time on-stream
[b]Two hour time on stream
[c]Dealuminized as in Example 1

EXAMPLE 9

A synthetic erionite catalyst was prepared from the following formulations:
 A. Sodium Aluminate Solution
  98.2 g NaAlO$_2$ (4.8 wt.% Al$_2$O$_3$, 33.1 wt.% Na$_2$O)
  1680 ml H$_2$O
  208 g NaOH 97 wt.%
  42.4 g KOH 85.5 wt.%
 B. Colloidal Silica
  234 g Colloidal Silica 30 wt.% SiO$_2$
 C. Benzyltrimethyl Ammonium Chloride
  142 g 60 wt.% solution These were mixed together adding C to A and then adding B. After mixing for 15 minutes the slurry was transferred to two polypropylene jars and reacted in a 212° F bath for 68 days. The crystalline synthetic erionite product had the following composition:

Na, wt.% — 2.3
K, wt.% — 4.7
N, wt.% — 0.77
$Al_2O_3$, wt.% — 14.1
$SiO_2$, wt.% — 81.0
Ash — 86.6

The adsorption capacity of a sample after calcination for 10 hours at 1000° F was:

Cyclohexane, wt.% — 1.0
n-Hexane, wt.% — 8.4
$H_2O$ — 16.6

Its surface area was 447 m²/gram.

The zeolite prepared above the calcined for 10 hours at 1000° F and then contacted 4 times with 113 ml of 0.5 N $NH_4Cl$ solution at 190°–195° F. The exchanged zeolite was water washed essentially free of chloride ion, dried at 230° F, pelleted and sized 14–25 mesh and then calcined for 10 hours at 1000° F prior to use. The residual sodium content was 0.18 wt.%.

EXAMPLE 10

Methanol at a rate of 7.6 ml. per hour was passed over 2 grams of a synthetic erionite prepared as in Example 9. The catalyst was contained in an 8 mm. outer diameter tubular glass reactor in the form of a 2⅞ inch bed. The catalyst was air calcined in place at 1000° F for one hour with an air flow of 10 cc/minute. Nitrogen at a rate of 10 cc/minute was passed over the bed for 10 minutes while the temperature was dropped to 700° F. The run conditions, temperature profile of the bed and the product analyses of reactor effluent samples, collected between 1 and 2 hours on-stream, are hereinafter set forth in Table III.

EXAMPLE 11

Zeolite T was prepared in accordance with Example 1 of U.S. Pat. No. 2,950,952. The resulting product had the following composition:

|   | Wt.% |
|---|---|
| Na | 2.07 |
| K | 8.18 |
| $Al_2O_3$ | 16.8 |
| $SiO_2$ | 67.7 |

Molar Ratio of $SiO_2/Al_2O_3$ 6.8

The sorption capacity of a sample calcined at 1000° F was as follows:

| Cyclohexane, wt.% | 0.6 |
|---|---|
| n-hexane, wt. % | 5.7 |
| $H_2O$ | 13.1 |

It had a surface area of 199 m²/gram.

The above alkali zeolite was subsequently processed by calcining in air for 10 hours at 1000° F then exchanged for 2 – 4 hour contacts with 5 Molar $NH_4Cl$ at 180° F using 6 ml of solution per essentially free of Cl-ion, drying and recalcining for 10 hours at 1000° F. The base exchange step was repeated again to reduce the residual alkali to low level. The water washed exchanged and recalcined for 10 hours at 1000° F.

An analysis of the final catalyst showed the following composition:

|   | Wt.% |
|---|---|
| Na | 0.075 |
| K | 1.65 |
| $Al_2O_3$ | 18.7 |
| $SiO_2$ | 78.8 |
| Molar Ratio $SiO_2/Al_2O_3$ | 7.2 |

EXAMPLE 12

Methanol at a rate of 7.5 ml/hour was passed over 2 grams of the catalyst prepared as in Example 11 under conditions essentially the same as those described in Example 10. Data are shown in Table III below.

TABLE III

| Example | 10 | 12 |
|---|---|---|
| Temp. Profile ° F |  |  |
| Inches from top 0 | 646 | 642 |
| ½ | 650 | 698 |
| 1 | 697 | 701 |
| 1½ | 713 | 705 |
| 2 | 706 | 717 |
| Hrs. on-Stream of |  |  |
| Temp. Profile | 2 | 2 |
| WHSV | 2.8 | 2.6 |
| Conversion (wt.%) | 11.1 | 3.3 |
| Hydrocarbon |  |  |
| Distribution (wt.%) |  |  |
| Methane | 3.6 | 2.1 |
| Ethane | 0.7 | 0 |
| Ethylene | 45.7 | 40.5 |
| Propane | 0 | 0 |
| Propylene | 30.0 | 22.1 |
| Butanes | 6.5 | 22.9 |
| Butenes | 10.0 | 7.4 |
| $C_5^+$ | 3.1 | 4.6 |

EXAMPLES 13 – 16

A supply of erionite ore was water washed for approximately 15 minutes and then air dried at about 40° C.

Methanol was pumped at a liquid hourly space velocity of 0.5 through a 1 gram bed of 14–30 mesh sample of the water-washed erionite. The reaction was carried out at temperatures of 370° C. and at atmospheric pressure. The hydrocarbon product distribution was determined by gas chromatography and the results set forth in Table IV below.

TABLE IV

| Example | 13 | 14 | 15 | 16 |
|---|---|---|---|---|
| Time on Stream (Minutes) | 55 | 100 | 135 | 190 |
| Conversion (Wt.%) | 27.4 | 13.2 | 7.7 | 3.8 |
| Hydrocarbon |  |  |  |  |
| Distribution (Wt.%) |  |  |  |  |
| Methane | 13 | 10.9 | 12.5 | 13.9 |
| Ethane | 0.2 | 0.8 | 2.0 | 3.5 |
| Ethylene | 22 | 28.4 | 30.2 | 28.8 |
| Propane | 8.7 | 14.4 | 15.3 | 8.9 |
| Propylene | 31.9 | 30.4 | 27.1 | 26.4 |
| Butanes | 5.7 | 2.7 | 3.8 | 4.1 |
| Butenes | 10.3 | 8.6 | 8.3 | 11.5 |
| $C_5^+$ | 8.2 | 3.8 | 0.8 | 2.9 |

It will be evident from the above results that ethylene and propylene were selectively produced utilizing the small pore crystalline aluminosilicate catalyst described herein.

EXAMPLE 17

Methanol at a rate of 0.9 cc/hour was passed over a 1 gram sample of 14–30 mesh calcium zeolite A, i.e. zeolite 5A, at 842° F. Conversion to hydrocarbons was 14 percent. The hydrocarbon product had the following composition:

|  | Weight Percent |
|---|---|
| Methane | 55.4 |
| Ethane | 5.2 |
| Ethylene | 12.3 |
| Propane | 3.3 |
| Propylene | 13.1 |
| Butanes | 1.1 |
| Butenes + $C_5^+$ | 9.6 |

It will be seen from the above results that the calcium 5A zeolite, while having the requisite pore size, did not achieve the selective production of ethylene and propylene as was realized with the zeolite catalysts described hereinabove contemplated for use in the process of this invention. Thus, the calcium 5A zeolite produced a predominate amount of methane, greatly in excess of that obtained utilizing the zeolite catalysts described hereinabove as being useful in the present process.

EXAMPLE 18

Mordenite (Norton Zeolon Type 100 H) was air calcined for one hour at 600° C. The material refluxed for 20 hours with 0.5 Normal HCl (50 ml solution per gram of zeolite), and then refluxed 20 hours with distilled water. The silica to alumina ratio of the resulting dealuminized mordenite, having pores in excess of 6 Angstroms, was 93.

Methanol was passed over a sample of the above material at a liquid hourly space velocity of 1 at a temperature of 700° F. and a pressure of 1 atmosphere. Conversion to hydrocarbon was 68.5 percent. The hydrocarbon product had the following composition:

|  | Weight Percent |
|---|---|
| Methane | 4.5 |
| Ethane | 0.3 |
| Ethylene | 11.0 |
| Propane | 5.9 |
| Propylene | 15.7 |
| Butanes | 13.8 |
| Butenes | 9.8 |
| $C_5^+$ Aliphatics | 18.5 |
| Aromatics | 20.5 |

It will be evident from the above results that while the dealuminized mordenite produced an amount of methane falling within the confines of the process of this invention, it was not a suitable catalyst in that it did not possess the requisite pore size characteristics and gave rise to an undesired production of aromatics to the detriment of ethylene and propylene production.

EXAMPLE 19

A 20 gram sample of the sodium form of zeolite Y (9% Na, $SiO_2/Al_2O_3 = 5.6$) was added to 100 ml of 1 normal tetraethylammonium bromide, heated to 88° C. and allowed to exchange 22 hours with mild agitation. The product was washed until free of halide, calcined in air at 2° F./min. to 1000° F., and then held at 1000° F. for 10 hours. The catalyst so treated lost 10 percent of its sodium through exchange to yield a resulting product of NaHY having pores in excess of 6 Angstroms.

Methanol was passed over a sample of the above material at a liquid hourly space velocity of 1 at a temperature of 700° F. and a pressure of 1 atmosphere. Conversion to hydrocarbon was 7.6 percent. The hydrocarbon product had the following composition:

|  | Weight Percent |
|---|---|
| Methane | 51.5 |
| Ethane | 6.1 |
| Ethylene | 7.6 |
| Propane | 1.5 |
| Propylene | 16.4 |
| Butanes | 1.4 |
| Butenes | 12.0 |
| $C_5^+$ Aliphatics | 2.7 |
| Aromatics | 0.8 |

It will be seen from the above results that use of the NaHY catalyst failed to achieve the desired selective production of ethylene and propylene. This catalyst not only did not have the requisite pore size characteristics but produced a predominate amount of methane.

It is to be understood that the foregoing description is merely illustrative of preferred embodiments of the invention of which many variations may be made by those skilled in the art within the scope of the following claims without departing from the spirit thereof.

We claim:

1. A catalytic process for converting a charge consisting essentially of methanol, dimethyl ether or mixtures thereof to a hydrocarbon product rich in ethylene and propylene which comprises contacting said charge under conversion conditions including a temperature between about 500° F and about 1100° F, a pressure from about 0.2 to 30 atmospheres and a liquid hourly space velocity of between about 0.1 and about 200 with a catalyst comprising a crystalline aluminosilicate zeolite characterized by pores, the major dimension of which is less than 6 Angstroms, further characterized by pore windows of about a size such as would be provided by 8-membered rings of oxygen atoms and the capability, under said conditions, of producing less than 20 weight percent methane in said hydrocarbon product.

2. The process of claim 1 wherein ethylene and propylene constitute a major proportion of the reaction product.

3. The process of claim 1 wherein the amount of ethylene and propylene produced is in excess of 35 weight percent and the amount of methane produced is not more than 10 weight percent of the reaction product.

4. The process of claim 1 wherein at least 10 percent of the cationic sites of said crystalline aluminosilicate zeolite are occupied by ions other than alkali or alkaline earth metals.

5. The process of claim 4 wherein said ions are ammonium, hydrogen, rare earth or combinations thereof.

6. The process of claim 1 wherein said crystalline aluminosilicate zeolite is predominantly in the hydrogen form.

7. The process of claim 1 wherein said crystalline aluminosilicate zeolite is contained in a matrix therefor.

8. The process of claim 1 wherein said crystalline aluminosilicate zeolite is erionite.

9. The process of claim 1 wherein said crystalline aluminosilicate zeolite is chabazite.

10. The process of claim 1 wherein said crystalline aluminosilicate zeolite is zeolite T.

11. The process of claim 1 wherein said crystalline aluminosilicate zeolite is dealuminized erionite.

12. The process of claim 1 wherein said crystalline aluminosilicate zeolite is ZK-5.

* * * * *

UNITED STATES PATENT AND TRADEMARK OFFICE
CERTIFICATE OF CORRECTION

PATENT NO. : 4,062,905
DATED : December 13, 1977
INVENTOR(S) : CLARENCE D. CHANG, WILLIAM H. LANG and ANTHONY J. SILVESTRI It is certified that error appears in the above-identified patent and that said Letters Patent are hereby corrected as shown below:

Column 7, line 28, "2 7/8" should be --2 1/8--;
Column 7, line 49, Line 49 should be included as last line in above table. And "SIO$_2$" should be --SiO$_2$--;
Column 9, line 9, "1.1" after the word "Butanes" in first column should be in second column of table.

Signed and Sealed this

Thirtieth Day of May 1978

[SEAL]

Attest:

RUTH C. MASON
Attesting Officer

LUTRELLE F. PARKER
Acting Commissioner of Patents and Trademarks